(12) United States Patent
Sivarajan et al.

(10) Patent No.: US 7,413,907 B2
(45) Date of Patent: Aug. 19, 2008

(54) CARBON NANOTUBES AND THEIR DERIVATIVES AS MATRIX ELEMENTS FOR THE MATRIX-ASSISTED LASER DESORPTION MASS SPECTROMETRY OF BIOMOLECULES AND SEQUENCING USING ASSOCIATED FRAGMENTATION

(75) Inventors: Ramesh Sivarajan, Medford, MA (US); Robert H. Hauge, Houston, TX (US); Terry Marriott, Houston, TX (US)

(73) Assignee: William Marsh Rice University, Houston, TX (US)

( * ) Notice: Subject to any disclaimer, the term of this patent is extended or adjusted under 35 U.S.C. 154(b) by 806 days.

(21) Appl. No.: 10/900,571

(22) Filed: Jul. 28, 2004

(65) Prior Publication Data
US 2005/0277201 A1 Dec. 15, 2005

Related U.S. Application Data

(60) Provisional application No. 60/490,563, filed on Jul. 28, 2003.

(51) Int. Cl.
*G01N 24/00* (2006.01)
(52) U.S. Cl. .................................................. 436/173
(58) Field of Classification Search .................. None
See application file for complete search history.

(56) References Cited

U.S. PATENT DOCUMENTS 7,256,394 B2 * 8/2007 Yang et al. .................. 250/288

OTHER PUBLICATIONS

Xu et al. "Carbon Nanotubes as Assisted Matrix for Laser Desorption/Ionization Time-of-Flight Mass Spectrometry", Anal. Chem., Nov. 15, 2003, v. 75, pp. 6191-6195.*

Chen et al. "Carbon Nanotubes as Affinity Probes for Peptides and Proteins in MALDI MS Analysis", J. Am. Soc. Mass Spectrom., 2004, v. 15, No. 11, pp. 1629-1635.*

Chen et al. "Integration of ion-exchange chromatography fractionation with reversed-phase liquid chromatography-atmospheric pressure chemical ionization mass spectrometer . . . ", J. Chromat. A, 2005, v. 1089, 87-100.*

Hu et al. "Matrix-Assisted Laser Desorption/Ionization Time-of-Flight Mass Spectrometry with a Matrix of Carbon Nanotubes for the Analysis of Low-Mass Compounds in Environmental Samples", Environ. Sci. Technol., 2005, v. 39, pp. 8442-8447.*

Ren et al. "Immobilized Carbon Nanotubes as Matrix for MALDI-TOF-MS Analysis: Applications to Neutral Small Carbohydrates", J. Am. Soc. Mass Spectrom., 2005, v. 16, pp. 333-339.*

Najam-ul-Haq et al. "Chemically modified carbon nanotubes as material enhanced laser desorption ionization (MELDI) material in protien profiling", Anal. Chim. Acta, 2006, v. 561, pp. 32-39.*

Ugarov et al. "MALDI Matrices for Biomolecular Analysis Based on Functionalized Carbon Nanomaterials", Anal Chem., 2004, v. 76, pp. 6734-6742.*

M. Karas, et al., "Laser Desorption Ionzation of Proteins with Molecular Masses Exceeding 10 000 Daltons", 60 Anal. Chem. (1988). pp. 2299-2301.

R.C. Beavis., "Matrix-Assisted Ultraviolet Laser Desorption: Evolution and Principles", 27 Org. Mass.Spec. (1992), pp. 653-659.

(Continued)

*Primary Examiner*—Yelena G Gakh
(74) *Attorney, Agent, or Firm*—Robert C. Shaddox; Winstead, P.C.

(57) ABSTRACT

The present invention is directed toward novel matrix elements, generally comprising functionalized carbon nanotubes, for matrix-assisted laser desorption ionization (MALDI)-mass spectroscopy (MS), methods of making such matrix elements, and to methods of using such matrix elements in MALDI-MS applications, particularly for the analysis of biological molecules. In some embodiments, by carefully tuning the absorption characteristics of the matrix element, biomolecular analytes can be sequenced.

25 Claims, 7 Drawing Sheets

OTHER PUBLICATIONS

R. Zenobi, et al., "Ion Formation in MALDI Mass Spectometry", 17 Mass. Spec.Rev. (1998), pp. 337-366.

M. Karas, et al., "Matrix-Assisted Laser Desorption/Ionization Mass Spectomerty of Biopolymers", 63 Anal.Chem. (1991), pp. 1193A-1203A.

H.S. Creel., "Prospects for the Analysis of High Molar Mass Polymers Using MALDI Mass Spectometry", 1 Trends. pol.Sci. (1993), pp. 336-342.

W.D. Bowers, et al., "Fragmentation of Oligopeptide Ions Using Ultraviolet Laser Radiation and Fourier Transform Mass Spectrometry", 106 J.Am.Chem.Soc. (1984), pp. 7288-7289.

K. Biemann et al., "How to Obtain and How to Use Mass Spectral Data at High Mass", Mass Spectrometry in the Analysis of Large Molecules, C.J. McNeal, ed. (Wiley, Chichester, 1986).

K. Biemann, et al., "Characterization by Tandern Mass Spectrometry of Structural Modifications in Proteins", 237 Science (1987), pp. 992-998.

M. Karas, et al., "Matrix-Assisted Ultraviolet Laser Desorption of Non-Volatile Compounds", 78 Int. J. Mass.Spectrm. Ion. Proc. (1987), pp. 53-68.

Iijima, "Helical microtubules of graphic carbon", Nature 354 (1991), pp. 56-58.

Iijima, et al., "Single-shell carbon nanotubes of 1-nm diameter", 363 Nature (1993), pp. 603-605.

Bethune et al., "Cobalt-catalysed growth of carbon nanotubes with single-atomic-layer walls", 363 Nature (1993), pp. 605-607.

Baughman et al., "Carbon nanotubes—the Route Toward Applications" 297 Science (2002), pp. 787-792.

S. Ramesh et al., "Identification of Large Fullerenes Formed During the Growth . . ." 107 J. Phys.Chem B (2003), pp. 1360-1365.

Liu et al., "Fullerene Pipes," 280 Science (1998), pp. 1253-1256.

Khabasheshku, et al. Chemistry of Carbon Nanotubes, Encycl. of Nanoscience and Nanotechnology, Ed. S. Nalwa, American Scientific Publishers, vol. 1, (2004) pp. 849-861.

Khabasheku, et al., "Fluorination of Single-Wall Carbon Nanotubes and Subsequent Derivatization . . . ". 35 J. L. Acc. Chem. Res. (2002), pp. 1087-1095.

Bahr, J. L., et al., "Covalent chemistry of single-wall carbon nanotubes", 12 J. Mater. Chem. (2002), pp. 1952-1958.

Georgakilas, V. et al., "Organic Functionalization of Carbon Nanotubes," 124 J. Am. Chem. Soc. (5) (2002), pp. 760-761.

Bachilo et al., "Structure-Assigned Optical Spectra of Single-Walled Carbon Nanotubes", 298 Science (2002), pp. 2361-2366.

Strano et al., "Electronic Structure Control of Single-Wall Carbon Nanotube Functionalization" 301 Science (2003), pp. 1519-1522.

J. Chen, et al., "Solution Properties of Single-Walled Carbon Nanotubes" 282 Science (1998), pp. 95-98.

M.J. O'Connell et al., "Band Gap Fluorescence from Individual Single-walled Carbon Nanotubes", 297 Science (2002), pp. 593-596.

Yakobson, et al., "Fullerene Nanotubes: C1,000,000 and Beyond", 85 American Scientist (1997), pp. 324-337.

A. Hirsch, "Functionalization of Single-Walled Carbon Nanotubes", 41 Angew. Chem.Int.Ed. (2002), pp. 1853-1859.

* cited by examiner 2,5-Dihydroxy
benzoic acid (DHB)

3,5-Dimethoxy-4-hydroxy
cinnamic acid

3-Hydroxypicolinic acid

Picolinic acid

4-Hydroxy-α-cyanocinnamic acid 2-(4-Hydroxyphenylazo)-
benzoic acid

CARBON NANOTUBES AND THEIR DERIVATIVES AS MATRIX ELEMENTS FOR THE MATRIX-ASSISTED LASER DESORPTION MASS SPECTROMETRY OF BIOMOLECULES AND SEQUENCING USING ASSOCIATED FRAGMENTATION

CROSS REFERENCE TO RELATED APPLICATIONS

This Application claims priority to U.S. Provisional Patent Application Ser. No. 60/490,563, filed Jul. 28, 2003.

The present invention was made with support from the National Science Foundation, Grant No. DMR-0073046; the Office of Naval Research, N00014-01-1-0789; and the National Aeronautics and Space Administration, Grant No. JSC NCC 9-77.

FIELD OF THE INVENTION

The present invention relates generally to mass spectrometry, and more specifically to the use of fullerene-based materials as matrix elements for matrix-assisted laser desorption mass spectrometry.

BACKGROUND OF THE INVENTION

The MALDI-MS technique, or Matrix-Assisted Laser Desorption Ionization Mass Spectrometry [M. Karas, F Hillencamp., *Anal. Chem.*, 60, 2301 (1988); R. C. Beavis., *Org. Mass. Spec.*, 27, 653 (1992)], has emerged as a powerful analytical tool in the investigation of non-volatile high molecular weight compounds, especially fragile biological molecules. Such techniques are simply referred to as "MALDI" herein. In the matrix-assisted laser desorption process, the anaylate is mixed with a matrix, usually a small organic molecule, at mole ratios of few thousand matrix molecules to the analyte. During irradiation with a laser, the matrix molecules assist in the desorption of the analyte molecule as molecular ions, as shown in FIG. 1. The mechanistic aspects of the interaction of the matrix molecules and the anaylate during irradiation has been a topic of continuing research [R. Zenobi, R. Knochenmuss, *Mass. Spec. Rev.*, 17, 337 (1998)]. MALDI is a soft-ionization technique, where the energy from the incident laser radiation is utilized to desorb the small molecules rather than dissociating the anaylate.

One of the key issues in MALDI analysis is the selection and availability of the right matrix molecule. The matrix molecule, in its assisting role, is expected to function as an efficient absorber of laser energy—as well to isolate the polymer molecules from one another [M. Karas, F. Hillencamp, R. C. Beavis, B. T. Chait., *Anal. Chem.*, 63, 1193A (1991); H. S. Creel., *Trends. Pol. Sci.*, 1, 336 (1993)]. While the purpose of the matrix is to desorb the anaylate without degradation, there is a positive aspect to fragmentation, especially when the anaylate is a biomolecule such as a peptide, protein or DNA.

Tandem mass spectrometry (TMS), in the recent past, has been developed into an efficient technique for solving the structural problems and sequencing of proteins and DNA molecules [W. D. Bowers, S. S. Delbert, R. L. Hunter, R. T. McIver., *J. Am. Chem. Soc*, 106, 7288 (1984); K. Biemann et al., in *Mass Spectrometry in the Analysis of Large Molecules*, C. J. McNeal ed (Wiley, Chichester, 1986)]. The schematics of tandem mass spectrometry are shown in FIG. 2. Referring to FIG. 2, a combination of biomolecules are ionized by fast ion bombardment at stage A, after which they pass through the first mass selector ($M_1$). The mass selected species then passes to the collision chamber (CS) where fragmentation is achieved through collision-induced decomposition (CID). The mass distribution of the fragments is analyzed in a second mass spectrometer ($M_2$) and a detector (D) to generate a CID-MS spectrum. The applications of tandem mass spectrometry in the sequencing of biomolecules has recently been reviewed by Biemann and Scoble [K. Biemann, H. A. Scoble., *Science*, 237, 992 (1987)].

A look at the fundamentals of both these techniques reveal that a matrix with properties tunable from one extreme of complete analyte desorption to the other extreme of complete fragmentation of the analyte can combine the advantages of both MALDI and TMS in a single technique. This requires a unique matrix element that is an efficient absorber in the ultraviolet (UV) region of the electromagnetic (EM) spectrum, and which can go through photo-ionization followed by excited state proton transfer (ESPT) [M. Karas, D. Bachmann, U. Bahr, F. Hillenkamp., *Int. J. Mass. Spectrm. Ion. Proc.*, 78, 53 (1987)]. The ESPT process requires the presence of labile protons in the matrix molecule. Some of the traditional matrix molecules are shown in FIG. 3. A common characteristic of all these matrix molecules is the presence of a labile, acidic proton in their molecular structure.

BRIEF DESCRIPTION OF THE INVENTION

The present invention is directed toward novel matrix elements, comprising carbon nanotubes, for matrix-assisted laser desorption ionization (MALDI)-mass spectroscopy (MS), methods of making such matrix elements, and to methods of using such matrix elements in MALDI-MS applications, particularly for the analysis of biological molecules. Generally, such CNTs are functionalized in some manner.

Generally, the present invention provides a new application for an existing material, viz., single-walled carbon nanotubes (SWNT) and derivatives thereof. The invention relies on their use as matrix elements in MALDI techniques, especially for biomolecules. The present invention surpasses the existing, conventional matrices in its ability to determine the fragment as well as the molecular ion. This is an important step in sequencing biomolecules like peptides.

As discussed above, one of the key issues in MALDI analysis is the selection and availability of the right matrix molecule. The matrix molecule, in its assisting role, is expected to function as an efficient absorber of laser energy as well to isolate the analyte molecules from one another.

A look at the fundamentals of MALDI and tandem mass spectrometry (TMS) reveal that a matrix element (material) with properties tunable from one extreme of complete analyte desorption to the other extreme of complete fragmentation of the analyte can combine the advantages of both MALDI and TMS into a single technique. This requires a unique matrix element that is an efficient absorber in the UV region and which can go through photoionization followed by excited state proton transfer (ESPT). The ESTP process requires the presence of labile protons in the matrix molecule. One of the common characteristic the conventional matrix molecules is the presence of a labile, acidic proton in their molecular structure.

In some embodiments of the present invention, single-walled carbon nanotubes (SWNTs) are utilized as such a unique and efficient matrix element because of their excellent UV absorption characteristics and their ability to be derivatized with functional groups of choice-thereby permitting tunability. Herein, Applicants demonstrate the potential of single-walled carbon nanotubes and their derivatives as candidates for the fragmentive dissociation of biomolecules such as peptides and proteins that would enable their sequencing.

In some embodiments, the present invention is drawn to a method comprising the following steps: 1) synthesis and purification of single-walled carbon nanotubes and formation of a thin SWNT mat (bucky paper) matrix material; 2) making a solution of the analyte molecules in a suitable solvent; 3) placing drops of the solution of analyte molecules on the SWNT mat and drying to remove the solvent; 4) mounting the SWNT mat onto a stainless steel sample holder; and 5) recording of the MALDI-TOF mass spectra.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
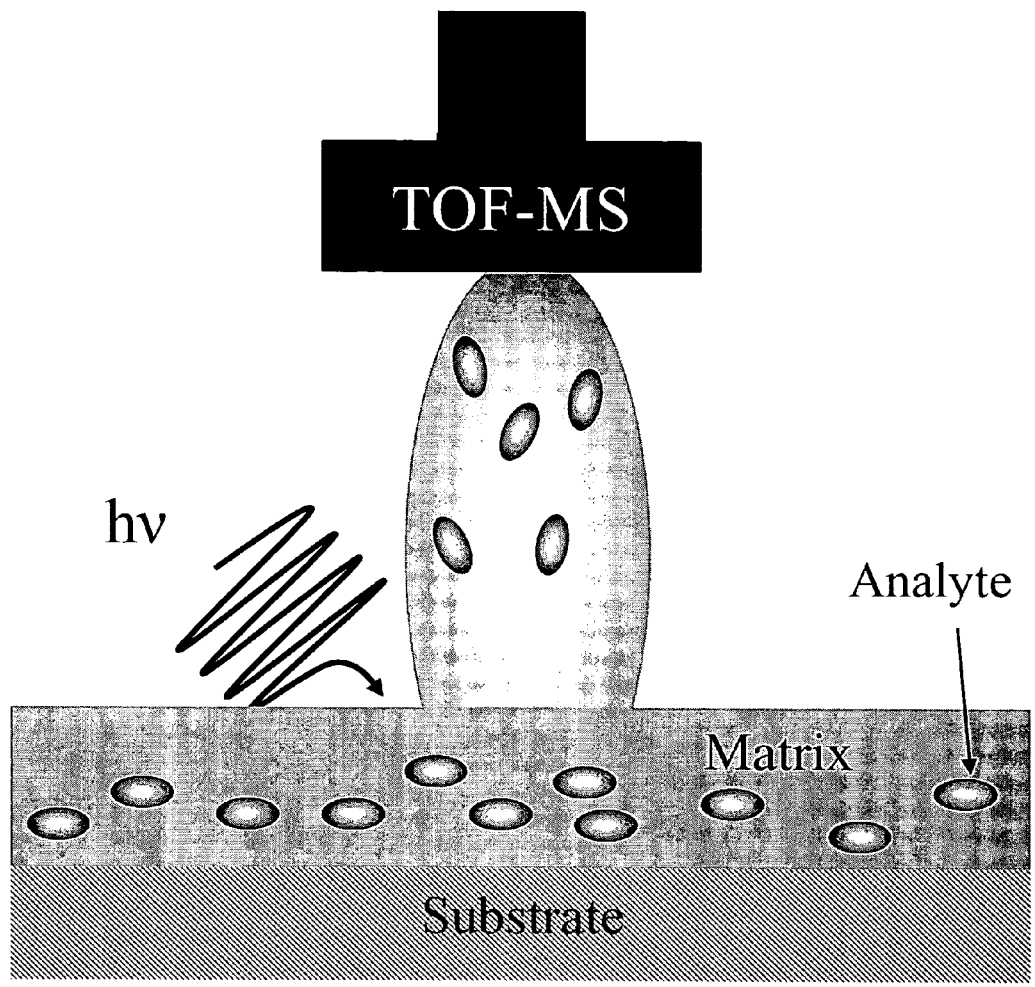
FIG. 1 illustrates the MALDI process, wherein matrix molecules assist in the desorption of the analyte molecules as molecular ions.
Figure 2:
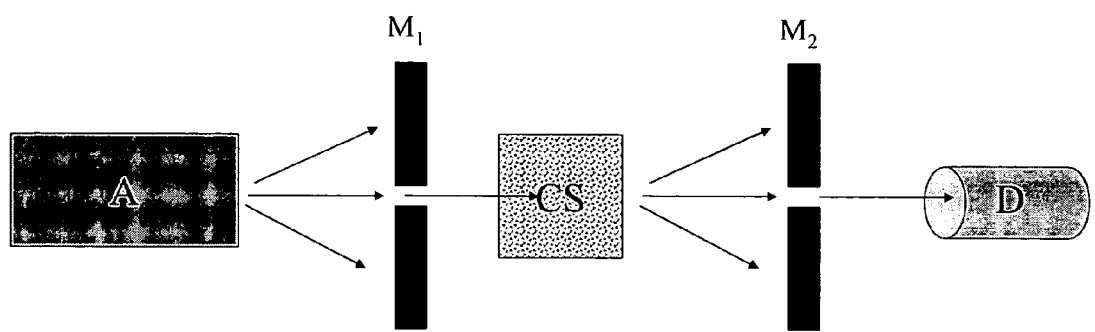
FIG. 2 illustrates the general elements of tandem mass spectrometry.
Figure 3:
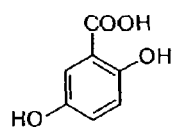
FIG. 3 depicts some of the molecules traditionally used as matrix material for MALDI.
Figure 3:
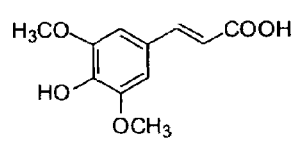
Figure 3:
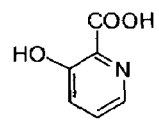
Figure 3:
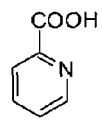
Figure 3:
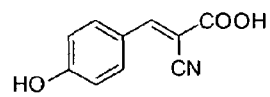
Figure 3:
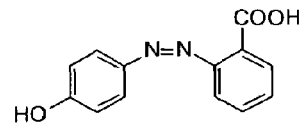

The present invention is directed toward novel matrix elements, comprising carbon nanotubes, for matrix assisted laser desorption ionization (MALDI)-mass spectroscopy (MS), methods of making such matrix elements, and to methods of using such matrix elements in MALDI-MS applications, particularly for the analysis of biological molecules.

Carbon nanotubes (CNTs), comprising multiple concentric shells and termed multi-wall carbon nanotubes (MWNTs), were discovered by Iijima in 1991 [Iijima, Nature, 354, 56 (1991)]. Subsequent to this discovery, single-wall carbon nanotubes (SWNTs), comprising a single graphene rolled up on itself, were synthesized in an arc-discharge process using carbon electrodes doped with transition metals [Iijima, S.; Ichihashi, T. Nature, 363, 603 (1993); and Bethune et al., Nature, 363, 605 (1993)]. These carbon nanotubes (especially SWNTs) posses unique mechanical, electrical, thermal and optical properties, and such properties make them attractive for a wide variety of applications. See Baughman et al., Science, 297, 787-792 (2002).

In some embodiments, the present invention is drawn to a method comprising the following steps: 1) functionalization of SWNTs to form functionalized SWNTs; 2) formation of a mat or 'bucky paper' of the functionalized SWNTs to serve as a matrix material; 3) making a solution of analyte molecules in a suitable solvent; 4) placing drops of the solution of analyte molecules on the functionalized SWNT mat and drying to remove the solvent; 5) mounting the functionalized SWNT mat onto a MALDI sample holder; and 6) recording of the MALDI-TOF mass spectra.

In some embodiments, when the analyte molecule is a biomolecule such as a polypeptide or oligonucleotide, the molecular sequence (e.g., peptide sequence) can be constructed from the fragmentation pattern.

While most of the discussion herein regards primarily SWNTs, the present invention is not limited to SWNTs. Any carbon nanotubes will likely work, as should fullerene species in general. Using combinations of different fullerene species and functionalized forms of these species as matrix elements for MALDI-MS, instead of, or in addition to, SWNTs, should be construed as falling within the scope of the present invention. It is generally desirable, however, to use fullerene species that can be functionalized and/or contain labile protons. As such, SWNTs and their close cousins represented by the giant fullerenes [S. Ramesh et al., J. Phys. Chem B, 107, 1360 (2003)] hold great potential as matrix elements for the MALDI analysis of biomolecules.

In some embodiments, the functionalized SWNTs comprise proton-bearing functional groups. These proton-bearing functional groups include, but are not limited to, hydroxyl groups, carboxylic acid groups, amino groups, and combinations thereof. Such groups can be attached to the SWNTs via covalent and/or non-covalent (e.g., ionic bonding, physisorption, etc.) means. Such groups can be attached to the SWNTs directly, or they can be attached via molecular linkages (or a combination of the two), such molecular linkages typically being alkyl chains of varying lengths or other spacer groups. In some embodiments, the functionalization, particularly the attachment of hydroxyl and carboxylic acid moieties, is a result of oxidative treatments, such treatments often being employed in the purification of CNTs [Liu et al., "Fullerene Pipes," Science, 280, 1253-1256 (1998)].

While SWNT purification processes typically functionalize only the ends of carbon nanotubes, SWNTs can also be functionalized on their sidewalls. Such sidewall chemistry of SWNTs includes direct fluorination and subsequent derivatization, addition of radicals, carbenes and nitrenes as well as the 1,3-dipolar and electrophilic additions, and modification through van der Waals interactions with aromatic molecules or polymers. See Khabashesku, V. N.; Margrave, J. L. "Chemistry of Carbon Nanotubes" in *Encyclopedia of Nanoscience and Nanotechnology*, Ed. S. Nalwa, American Scientific Publishers, Vol. 1, pp. 849-861 (2004), and references therein; Khabashesku, V. N.; Billups, W. E.; Margrave, J. L. *Acc. Chem. Res.*, 35, 1087 (2002); Bahr, J. L.; Tour, J. M. *J. Mater. Chem.*, 12, 1952 (2002); Georgakilas, V. et al., "Organic Functionalization of Carbon Nanotubes," *J. Am. Chem. Soc.*, 124 (5), 760-761 (2002).

In some embodiments, the optical properties (i.e., UV absorption) of the SWNT-MALDI matrix material are tuned for optimal laser desorption/ionization of a particular analyte by careful selection of the type and amount of the functionalizing moiety on the functionalized SWNTs. In some or other embodiments, the laser excitation frequency can be modulated. Finally, in some or still other embodiments, the employment of organic and/or inorganic chromophores, co-adsorbed or covalently bonded to the SWNTs, can be used to alter and modify the UV absorption characteristics—not withstanding their chemical interaction with the analyte molecules.

In some embodiments, isolated or unique combinations of different types of SWNTs [Bachilo et al., *Science*, 298, 2361-2366 (2002)] may be employed in the SWNT-MALDI matrix. Indeed, such SWNTs can be selectively functionalized [Strano et al., *Science*, 301, 1519-1522 (2003)]. In some or other embodiments, combinations of functionalized SWNTs can be combined with other types of fullerene materials (functionalized or not) to more finely tune the absorption characteristics of the matrix element.

In some embodiments, the SWNTs and/or giant fullerenes are functionalized, using methods referenced above, with functional groups that are compatible with a photoionization and excited state proton transfer process. Generally, at least some of these groups are selected from the group consisting of hydroxyls, carboxylic acids, primary and secondary amino groups, and combinations thereof. Additionally, refluxing the SWNTs in mineral acids such as nitric or sulfuric acid enables derivatization of the edges and defects on the SWNT with carboxylic acid groups which could serve as a template for further derivatization [J. Chen, M. A. Hanmon, H. Hu, Y. Chen, A. M. Rao, P. C. Eklund, R. C. Haddon., *Science*, 282, 95 (1998)].

In some embodiments, the above-described methods can be extended for the molecular weight determination of water soluble polymers.

In some embodiments, the functionalized SWNT-MALDI matrix elements are supplied in the form of "ready to use" mats. In some embodiments, the composition of the mat is dependent upon the particular analyte species and the laser desorption wavelength. In this arrangement a small drop of sample will be placed on the mat, dried and then exposed to laser irradiation. This process will greatly enhance automation in the analysis of biomolecules by eliminating the laborious sample preparation step.

In some embodiments, the use of neat and/or derivatized carbon nanotubes and fullerenes are used in combination with conventional molecules in the MALDI matrix element.

In some embodiments, functionalized SWNTs comprising hydroxyls or carboxylic acid groups are used as efficient matrix elements in the matrix assisted fragmentive laser desorption of peptides, thereby enabling their sequencing. As shown in the Example that follows, MALDI spectra of Angiotensin II have been recorded as a with a SWNT matrix and compared with a conventional cyanocinnamic acid (CCA) matrix as a control. Fragments, as well the molecular ion, were observed in the case of the SWNT matrix and the known sequence was constructed from the fragments as a demonstration of sequencing potential. Chemical methods to derivatize the SWNT with carboxylic acid groups, amines and hydroxyls are suggested to increase the efficiency of the SWNT matrix.

The following Example is provided to more fully illustrate some of the embodiments of the present invention. It should be appreciated by those of skill in the art that the techniques disclosed in the Example which follows represent techniques discovered by the inventors to function well in the practice of the invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the invention.

EXAMPLE

Based on interesting UV absorption characteristics [M. J. O'Connell et al., *Science*, 297, 593 (2002)] and excellent mechanical properties, [B. I. Yakobson and R. E. Smalley., *American Scientist.*, 85, 324 (1997)]. Applicants demonstrate in this Example the extraordinary potential of single-walled carbon nanotubes (SWNT) as efficient, non-desorbing matrix elements for MALDI-MS. Applicants further highlight the potential of using SWNTs and their derivatives as promising candidates for the fragmentive dissociation of biomolecules, such as peptides and proteins, that would enable their sequencing. Angiotensin II, a polypeptide, has been used as a test case to verify the efficiency of SWNTs as matrices for laser desorption ionization.

MALDI experiments on the Angiotensin II were carried out under three different conditions. In the first case, tiny drops of the aqueous solution of the peptide were placed directly on stainless steel sample plate and dried. In the second case, a small circle (~5 mm diameter) of thin bucky paper of HiPco single-walled carbon nanotubes (HPR-106) cleaned of residual metal catalysts and laser desorbable carbons [S. Ramesh et al., *J. Phys. Chem B*, 107, 1360 (2003)] was attached to the stainless steel sample plate by double sided adhesive tape. A tiny drop of the Angiotensin II sample was placed on the bucky paper and allowed to dry at room temperature. In the third case, a sample of Angiotensin II in a cyanocinnamic acid (CCA) matrix was placed on the sample plate and allowed to dry. Laser desorption was carried out at different attenuations of laser power and time-of-flight mass spectra were recorded.

Figure 4:
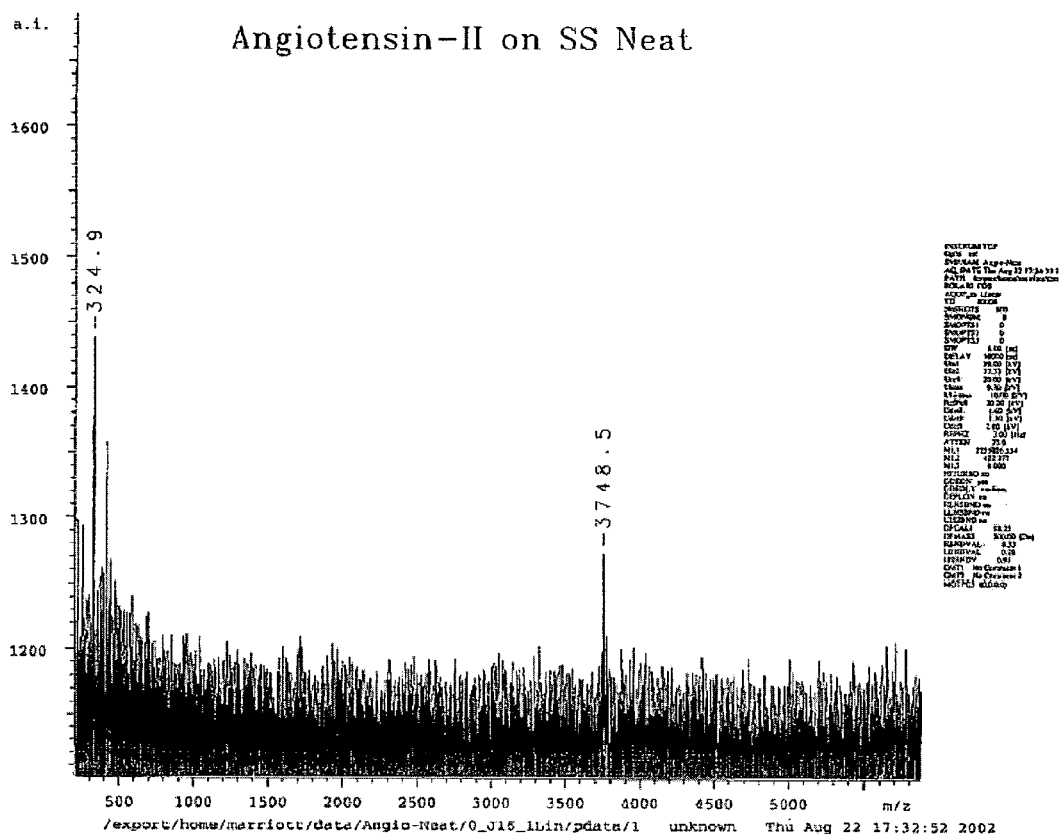
FIG. 4 depicts MALDI spectra of Angiotensin II obtained from neat analyte on a stainless steel plate.
Figure 5:
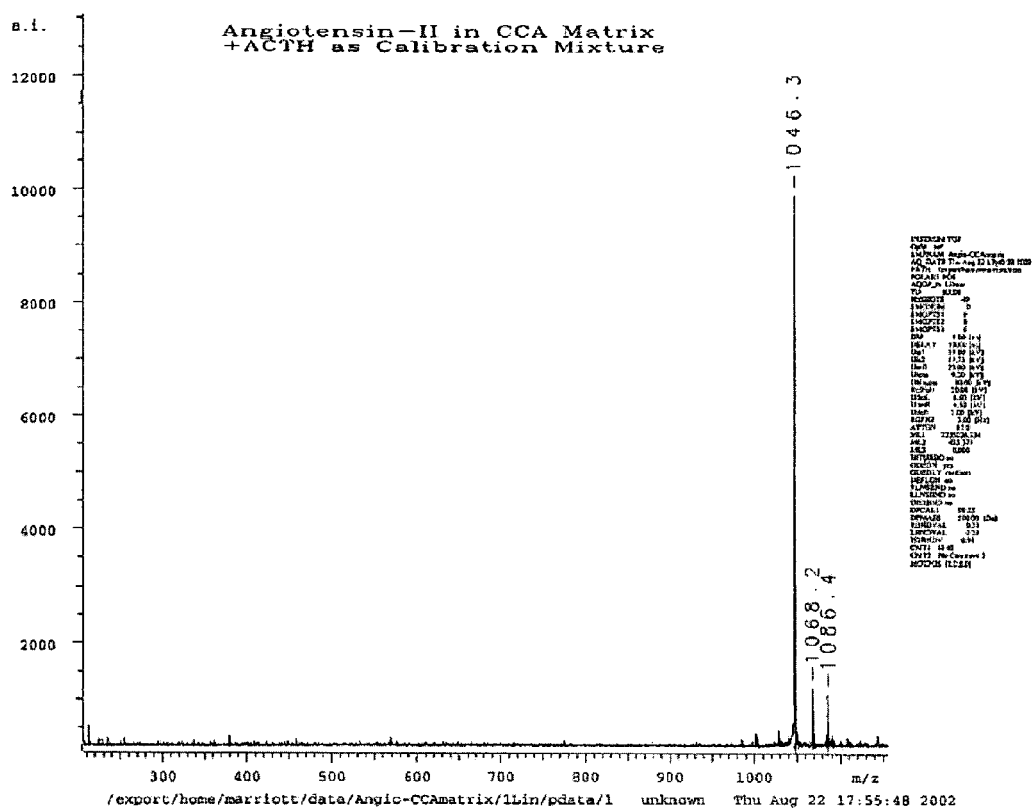
FIG. 5 depicts MALDI spectra of Angiotensin II obtained using CCA as the matrix element.
Figure 6:
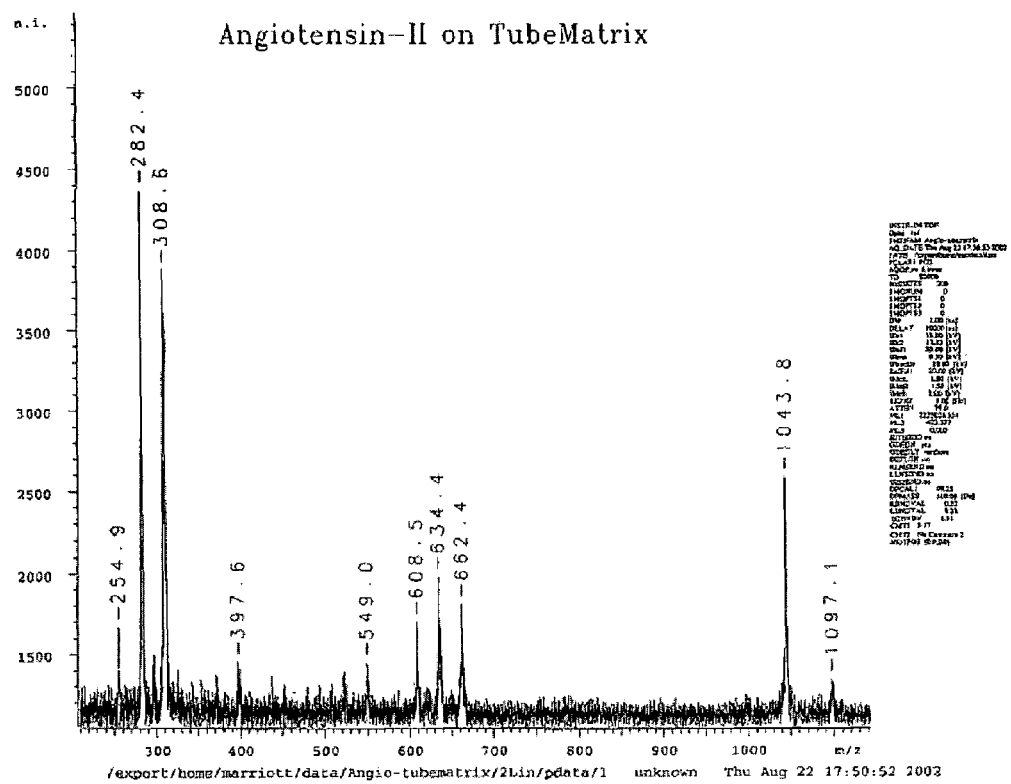
FIG. 6 depicts MALDI spectra of Angiotensin II obtained using SWNTs as the matrix element.
Figure 7:
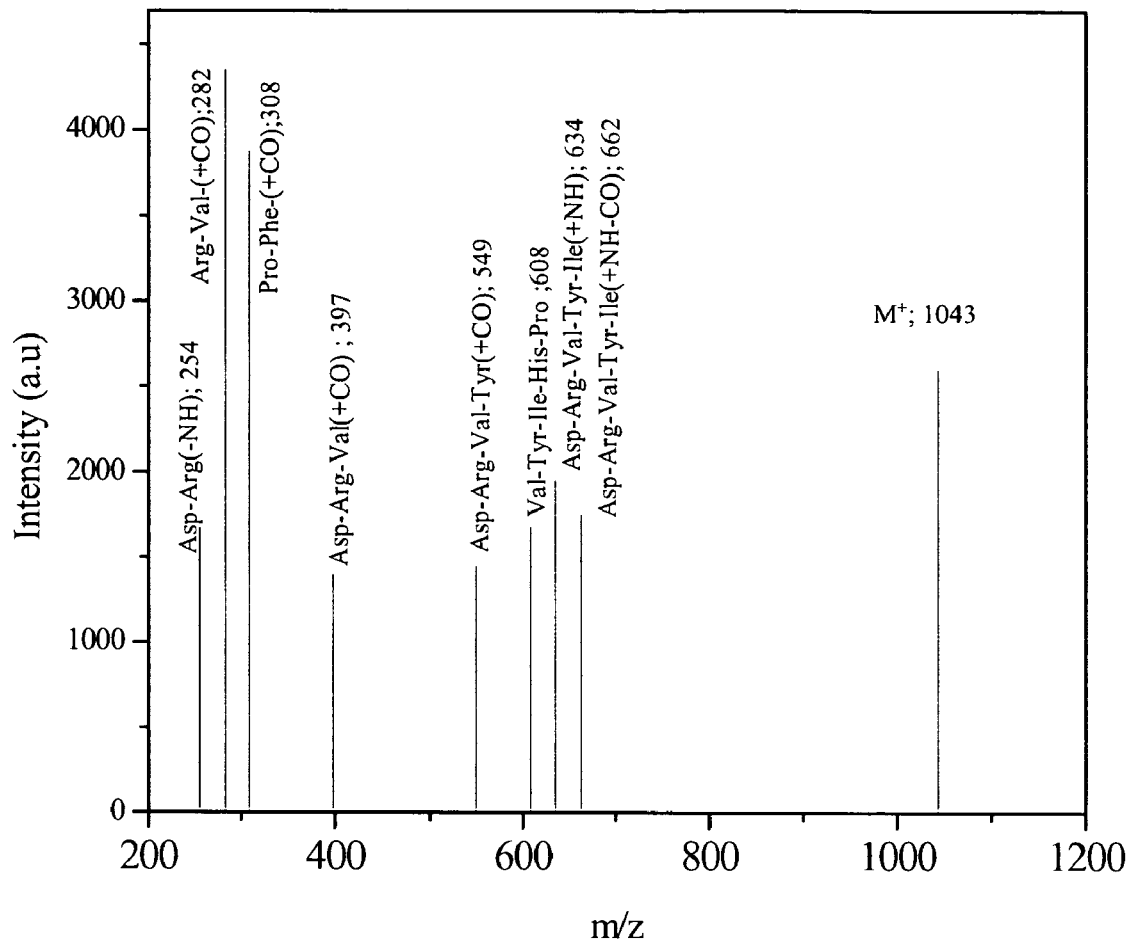
FIG. 7 depicts masses of fragments observed in the case of Angiotensin II being desorbed off a SWNT matrix.

MALDI spectra obtained under the above three experimental conditions are shown in FIGS. 4-6. FIG. 4, obtained in the case of a neat Angiotensin II sample on a stainless steel plate, did not give any detectable mass signal of the molecular ion or the angiotensin fragments. The spectra shown in FIG. 5 was recorded employing CCA as a matrix element with ACTH as the calibration mixture. The spectra shows both the molecular ions of Angiotensin II (1046 a.m.u) and ACTH (2466 a.m.u) (a.m.u. is acronym for atomic mass unit). The fragments of Angiotensin II or the calibrant were not fragmented. The signal strength of the angiotensin molecular ion at an attenuation of 87% was about 10,000 (arbitrary units). The mass spectra recorded in the case of Angiotensin II on a carbon nanotube matrix is shown in FIG. 6. The spectra shows the molecular ion at 1043 a.m.u., along with fragments at lower masses. The molecular ion is off by a few a.m.u. due to a minor reduction in the flight length caused by the thickness of the bucky paper and the adhesive tape. For the lower masses, the variation is less than one a.m.u. The lower mass fragments could be assigned to the fragments arising from the cleaving of the peptide bond in the Angiotensin II molecule which has a sequence of Asp-Arg-Val-Tyr-Ile-His-Pro-Phe. The masses of fragments observed in the case of Angiotensin II are shown in FIG. 7 along with the assignment for the corresponding mass peaks. A cursory look at the pattern suggests that an unknown peptide could also be sequenced from the masses of natural amino acids as in the case of tandem mass spectrometry [K. Biemann et al., in *Mass Spectrometry in the Analysis of Large Molecules*, C. J. McNeal ed (Wiley, Chichester, 1986)]. The primary point of interaction between the polypeptide and the SWNT is suggested to be the hydroxyls and carboxylic acid groups that are formed by the oxidative hydrolysis of the single-walled carbon nanotubes during the cleaning (purification) process [A. Hirsch, Angew. *Chem. Int. Ed.*, 41, 1853 (2002); J. Chen, M. A. Hanmon, H. Hu, Y. Chen, A. M. Rao, P. C. Eklund, R. C. Haddon., *Science*, 282, 95 (1998)].

Thus, single-walled carbon nanotubes have been used as a generic matrix element, for any sorbent, in desorption spectroscopy. They can, however, be tuned through functionalization or other means to be more efficient desorbers for one or more particular species. It is perhaps still more significant as they form an excellent matrix element for the fragmentive dissociation of biomolecules.

Herein, Applicants have demonstrated the potential of single-walled carbon nanotubes and their derivatives as promising candidates for the fragmentive dissociation of biomolecules such as peptides and proteins that would enable their sequencing. Angiotensin II, a polypeptide has been used as a test case to verify the efficiency of SWNT as matrices for laser desorption ionization.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed is:

1. A method for analyzing molecules with MALDI-MS comprising the steps of:
   a) providing a mat of functionalized carbon nanotubes;
   b) making a solution of analyte molecules in a suitable solvent;
   c) contacting the analyte molecules with the mat of carbon nanotubes by placing a quantity of the analyte solution on the mat;
   d) removing the solvent to form an analyte mat; and
   e) performing MALDI-MS on the analyte mat.

2. The method of claim 1, wherein the step of removing involves an evaporation of the solvent.

3. The method of claim 1, wherein the carbon nanotubes are selected from the group consisting of single-wall carbon nanotubes, multi-wall carbon nanotubes, double-wall carbon nanotubes, and combinations thereof.

4. The method of claim 1, wherein the functionalized carbon nanotubes comprise functional groups are associated with the carbon nanotubes via covalent bonding.

5. The method of claim 1, wherein the functionalized carbon nanotubes comprise functional groups are associated with the carbon nanotubes via at least one type of non-covalent bonding selected from the group consisting of ionic bonding, hydrogen bonding, van der Waals attractive forces, and combinations thereof.

6. The method of claim 1, wherein the functionalized carbon nanotubes possess functional groups selected from the group consisting of hydroxyl, carboxyl, carbonyl, amino, and combinations thereof.

7. The method of claim 1, wherein the functionalized carbon nanotubes comprise functional groups that provide labile protons.

8. The method of claim 1, wherein the functionalization is provided during an oxidative purification of the carbon nanotubes.

9. The method of claim 1, wherein the analyte molecules are polymeric.

10. The method of claim 1, wherein the analyte molecules are biomolecular.

11. The method of claim 1, wherein the analyte molecules are selected from the group consisting of polymers, oligomers, polypeptides, proteins; nucleic acids, and combinations thereof.

12. The method of claim 11, wherein the analyte molecules undergo fragmentation.

13. The method of claim 12, wherein the fragmentation permits sequencing of the analyte molecules.

14. The method of claim 1, wherein the step of performing MALDI-MS comprises affixing the analyte mat to the MALDI-MS sample holder.

15. A method for analyzing molecules with MALDI-MS comprising the steps of:
   a) providing a matrix material comprising functionalized carbon nanotubes;
   b) making a solution of analyte molecules in a suitable solvent;
   c) contacting the analyte molecules with the matrix material by placing a quantity of the analyte solution on the material;
   d) removing the solvent to form an analyte matrix; and
   e) performing MALDI-MS on the analyte matrix.

16. The method of claim 15, wherein the step of removing involves evaporation of the solvent.

17. The method of claim 15, wherein the carbon nanotubes are selected from the group consisting of single-wall carbon nanotubes, multi-wall carbon nanotubes, double-wall carbon nanotubes, and combinations thereof.

18. The method of claim 15, wherein the matrix material further comprises a fullerene material selected from the group consisting of functionalized fullerenes, unfunctionalized fullerenes, and combinations thereof.

19. The material of claim 15, wherein the functionalized carbon nanotubes comprise functional groups are associated with the carbon nanotubes via covalent bonding.

20. The material of claim 15, wherein the functionalized carbon nanotubes comprise functional groups are associated with the carbon nanotubes via at least one type of non-covalent bonding selected from the group consisting of ionic bonding, hydrogen bonding, van der Waals attractive forces, and combinations thereof.

21. The material of claim 15, wherein the functionalized carbon nanotubes possess functional groups selected from the group consisting of hydroxyl, carboxyl, amino, and combinations thereof, wherein such functional groups provide labile protons.

22. The method of claim 15, wherein the analyte molecules are polymeric species selected from the group consisting of polymers, oligomers, and combinations thereof.

23. The method of claim 15, wherein the analyte molecules are biomolecules selected from the group consisting of polypeptides, proteins, nucleic acids, and combinations thereof.

24. The method of claim 15, wherein the analyte molecules undergo fragmentation.

25. The method of claim 24, wherein the fragmentation permits sequencing of the analyte molecules.

* * * * *